(12) United States Patent
Xu et al.

(10) Patent No.: US 6,790,448 B2
(45) Date of Patent: Sep. 14, 2004

(54) SURFACE PROTEINS FROM GRAM-POSITIVE BACTERIA HAVING HIGHLY CONSERVED MOTIFS AND ANTIBODIES THAT RECOGNIZE THEM

(75) Inventors: Yi Xu, Houston, TX (US); Magnus A. O. Hook, Houston, TX (US)

(73) Assignee: The Texas A&M University System University, College Station, TX (US)

( * ) Notice: Subject to any disclaimer, the term of this patent is extended or adjusted under 35 U.S.C. 154(b) by 0 days.

(21) Appl. No.: 10/140,372

(22) Filed: May 8, 2002

(65) Prior Publication Data

US 2003/0021789 A1 Jan. 30, 2003

Related U.S. Application Data

(60) Provisional application No. 60/289,132, filed on May 8, 2001.

(51) Int. Cl.[7] .................. A01N 63/00; A61K 39/00; A61K 39/02; A61K 39/085; A61K 39/09
(52) U.S. Cl. ............... 424/190.1; 424/93.42; 424/165.1; 424/185.1; 424/190.1; 424/192.1; 424/237.1; 424/243.1; 424/278.1; 424/279.1; 435/7.33; 435/36; 530/300; 530/326; 530/387.9; 930/10; 930/20; 930/200; 930/290
(58) Field of Search ................ 424/169, 163.9, 424/164.1, 165.1; 436/86; 525/54.11; 530/300, 323, 324, 325, 326–330; 930/20, 190, 200

(56) References Cited

U.S. PATENT DOCUMENTS

| 5,175,096 A | 12/1992 | Hook et al. |
| 5,320,951 A | 6/1994 | Hook et al. |
| 5,416,021 A | 5/1995 | Hook et al. |
| 5,440,014 A | 8/1995 | Hook et al. |
| 5,571,514 A | 11/1996 | Hook et al. |
| 5,652,217 A | 7/1997 | Hook et al. |
| 5,707,702 A | 1/1998 | Brady, Jr. et al. |
| 5,789,549 A | 8/1998 | Hook et al. |
| 5,840,846 A | 11/1998 | Hook et al. |
| 5,851,794 A | 12/1998 | Guss et al. |
| 5,980,908 A | 11/1999 | Hook et al. |
| 6,008,341 A | 12/1999 | Foster et al. |
| 6,086,895 A | 7/2000 | Hook et al. |
| 6,177,084 B1 | 1/2001 | Foster et al. |
| 6,288,214 B1 | 9/2001 | Hook et al. |

OTHER PUBLICATIONS

Kuroda et al., "Whole genome sequencing of meticillin–resistant *Staphylococcus aureus*", The Lancet, vol. 357, Apr. 21, 2001, pp. 1225–1240.

Primary Examiner—Lynette R. F. Smith
Assistant Examiner—J. Hines
(74) Attorney, Agent, or Firm—Stites & Harbison PLLC; B. Aaron Schulman

(57) ABSTRACT

Isolated peptide sequences and proteins containing these sequences are provided which are useful in the prevention and treatment of infection caused by Gram-positive bacteria. The peptide sequences have been shown to be highly conserved motifs in the surface proteins of Gram-positive bacteria, and these consensus sequences include amino acid sequences such as LPXTG (SEQ ID NO:13), ALKTGKI-DIIISGMTSTPERKK (SEQ ID NO:14), VEGAWEKP-VAEAYLKQN (SEQ ID NO:15), and EYAGVDIDLAK-KIAK (SEQ ID NO:16). By virtue of the highly conserved regions, the sequences and the proteins including these sequences can be utilized to generate antibodies which can recognize these highly conserved motifs and the proteins containing them and thus be useful in the treatment or prevention of a wide range of infections caused by Gram-positive bacteria.

2 Claims, 2 Drawing Sheets

FIG. 1

FIG. 2

SEQUENCE LISTING

<160> NUMBER OF SEQ ID NOS: 16

<210> SEQ ID NO 1
<211> LENGTH: 400
<212> TYPE: PRT

-continued

<213> ORGANISM: Staphylococcus aureus

<400> SEQUENCE: 1

Met Asn Tyr Ser Ser Arg Gln Gln Pro Asp Lys His Trp Leu Arg Lys
1               5                   10                  15

Val Asp Trp Val Leu Val Ala Thr Ile Ala Val Leu Ala Ile Phe Ser
            20                  25                  30

Val Leu Leu Ile Asn Ser Ala Met Gly Gly Gln Tyr Ser Ala Asn
        35                  40                  45

Phe Gly Ile Arg Gln Ile Phe Tyr Tyr Ile Leu Gly Ala Ile Phe Ala
    50                  55                  60

Gly Ile Ile Met Phe Ile Ser Pro Lys Lys Ile Lys His Tyr Thr Tyr
65                  70                  75                  80

Leu Leu Tyr Phe Leu Ile Cys Leu Leu Leu Ile Gly Leu Leu Val Ile
                85                  90                  95

Pro Glu Ser Pro Ile Thr Pro Ile Ile Asn Gly Ala Lys Ser Trp Tyr
            100                 105                 110

Thr Phe Gly Pro Ile Ser Ile Gln Pro Ser Glu Phe Met Lys Ile Ile
        115                 120                 125

Leu Ile Leu Ala Leu Ala Arg Val Val Ser Arg His Asn Gln Phe Thr
    130                 135                 140

Phe Asn Lys Ser Phe Gln Ser Asp Leu Leu Phe Phe Lys Ile Ile
145                 150                 155                 160

Gly Val Ser Leu Val Pro Ser Ile Leu Ile Leu Gln Asn Asp Leu
                165                 170                 175

Gly Thr Thr Leu Val Leu Ala Ala Ile Ile Ala Gly Val Met Leu Val
            180                 185                 190

Ser Gly Ile Thr Trp Arg Ile Leu Ala Pro Ile Phe Ile Thr Gly Ile
        195                 200                 205

Val Gly Ala Met Thr Val Ile Leu Gly Ile Leu Tyr Ala Pro Ala Leu
    210                 215                 220

Ile Glu Asn Leu Leu Gly Val Gln Leu Tyr Gln Met Gly Arg Ile Asn
225                 230                 235                 240

Ser Trp Leu Asp Pro Tyr Thr Tyr Ser Ser Gly Asp Gly Tyr His Leu
                245                 250                 255

Thr Glu Ser Leu Lys Ala Ile Gly Ser Gly Gln Leu Leu Gly Lys Gly
            260                 265                 270

Tyr Asn His Gly Glu Val Tyr Ile Pro Glu Asn His Thr Asp Phe Ile
        275                 280                 285

Phe Ser Val Ile Gly Glu Glu Leu Gly Phe Ile Gly Ser Val Ile Leu
    290                 295                 300

Ile Leu Ile Phe Leu Phe Leu Ile Phe His Leu Ile Arg Leu Ala Ala
305                 310                 315                 320

Lys Ile Glu Asp Gln Phe Asn Lys Ile Phe Ile Val Gly Phe Val Thr
                325                 330                 335

Leu Leu Val Phe His Ile Leu Gln Asn Ile Gly Met Thr Ile Gln Leu
            340                 345                 350

Leu Pro Ile Thr Gly Ile Pro Leu Pro Phe Ile Ser Tyr Gly Gly Ser
        355                 360                 365

Ala Leu Trp Ser Met Met Thr Gly Ile Gly Ile Val Leu Ser Ile Tyr
    370                 375                 380

Tyr His Glu Pro Lys Arg Tyr Val Asp Leu Tyr His Pro Lys Ser Asn
385                 390                 395                 400

```
<210> SEQ ID NO 2
<211> LENGTH: 403
<212> TYPE: PRT
<213> ORGANISM: Staphylococcus epidermidis

<400> SEQUENCE: 2

Met Asn Tyr Ser Ser Arg Gln Gln Pro Lys Arg Asn Trp Leu Arg Lys
1               5                   10                  15

Val Asp Trp Ile Leu Val Leu Val Ile Ser Leu Leu Ala Leu Thr Ser
            20                  25                  30

Val Ile Leu Ile Ser Ser Ala Met Gly Gly Gly Gln Tyr Ser Ala Asn
        35                  40                  45

Phe Ser Ile Arg Gln Ile Ile Tyr Tyr Ile Phe Gly Ala Ile Ala
50                  55                  60

Phe Leu Ile Met Ile Ile Ser Pro Lys Lys Ile Lys Asn Asn Thr Tyr
65                  70                  75                  80

Ile Leu Tyr Ser Ile Phe Cys Val Leu Leu Ile Gly Leu Leu Ile Leu
                85                  90                  95

Pro Glu Thr Ser Ile Thr Pro Ile Ile Asn Gly Ala Lys Ser Trp Tyr
                    100                 105                 110

Ser Phe Gly Pro Ile Ser Ile Gln Pro Ser Glu Phe Met Lys Ile Ile
            115                 120                 125

Leu Ile Leu Ala Leu Ala Lys Thr Ile Ser Lys His Asn Gln Phe Thr
130                 135                 140

Phe Asn Lys Ser Phe Gln Ser Asp Leu Met Leu Phe Lys Ile Leu
145                 150                 155                 160

Gly Val Ser Ile Ile Pro Met Ala Leu Ile Leu Gln Asn Asp Leu
                165                 170                 175

Gly Thr Thr Leu Val Leu Cys Ala Ile Ile Ala Gly Val Met Leu Val
                    180                 185                 190

Ser Gly Ile Thr Trp Arg Ile Leu Ala Pro Leu Phe Ile Val Ala Phe
            195                 200                 205

Val Ser Gly Ser Ser Ile Ile Leu Ala Ile Ile Tyr Lys Pro Ser Leu
210                 215                 220

Ile Glu Asn Leu Leu Gly Ile Lys Met Tyr Gln Met Gly Arg Ile Asn
225                 230                 235                 240

Ser Trp Leu Asp Pro Tyr Ser Tyr Ser Ser Gly Asp Gly Tyr His Leu
                245                 250                 255

Thr Glu Ser Leu Lys Ala Ile Gly Ser Gly Gln Leu Leu Gly Lys Gly
                260                 265                 270

Tyr Asn His Gly Glu Val Tyr Ile Pro Glu Asn His Thr Asp Phe Ile
            275                 280                 285

Phe Ser Val Ile Gly Glu Glu Met Gly Phe Ile Gly Ser Val Leu Leu
290                 295                 300

Ile Leu Leu Phe Leu Phe Leu Ile Phe His Leu Ile Arg Leu Ala Ser
305                 310                 315                 320

Lys Ile Asp Ser Gln Phe Asn Lys Val Phe Ile Ile Gly Tyr Val Ser
                325                 330                 335

Leu Ile Val Phe His Val Leu Gln Asn Ile Gly Met Thr Val Gln Leu
            340                 345                 350

Leu Pro Ile Thr Gly Ile Pro Leu Pro Phe Ile Ser Tyr Gly Gly Ser
        355                 360                 365

Ser Leu Trp Ser Leu Met Thr Gly Ile Gly Val Val Leu Ser Ile Tyr
370                 375                 380
```

```
Tyr His Glu Pro Gln Arg Tyr Glu Ile Thr Thr Leu Ser Lys Lys Ser
385                 390                 395                 400

Asn Thr Ile

<210> SEQ ID NO 3
<211> LENGTH: 408
<212> TYPE: PRT
<213> ORGANISM: Streptococcus mutans

<400> SEQUENCE: 3

Met Ala Ser Lys Lys Pro Ile Asp Ser Arg Val Asp Tyr Ser Leu
1               5                   10                  15

Ile Leu Pro Val Phe Phe Leu Val Leu Ile Gly Leu Phe Ser Val Tyr
                20                  25                  30

Thr Ala Thr Ile His Asp Tyr Pro Ser Lys Ile Met Val Val Met Gly
            35                  40                  45

Gln Gln Leu Ile Trp Leu Ile Met Gly Ala Ala Ile Ser Phe Val Val
        50                  55                  60

Met Leu Phe Ser Thr Glu Phe Leu Trp Lys Ile Thr Pro Tyr Leu Tyr
65                  70                  75                  80

Gly Leu Gly Leu Ile Leu Met Ile Phe Pro Leu Ile Phe Tyr Ser Pro
                85                  90                  95

Glu Leu Val Ala Ser Thr Gly Ala Lys Asn Trp Val Ser Ile Gly Ser
            100                 105                 110

Val Thr Leu Phe Gln Pro Ser Glu Phe Met Lys Ile Ser Tyr Ile Leu
        115                 120                 125

Ile Leu Ala Arg Leu Thr Val Thr Phe Lys Gln Lys Tyr Lys Glu Lys
130                 135                 140

Asn Leu Gln Glu Asp Gly Lys Leu Leu Leu Trp Phe Ala Leu Leu Thr
145                 150                 155                 160

Leu Pro Ile Met Ile Leu Leu Ala Leu Gln Lys Asp Leu Gly Thr Ala
                165                 170                 175

Met Val Phe Met Ala Ile Leu Ala Gly Leu Val Leu Ile Ala Gly Ile
            180                 185                 190

Ser Trp Gln Ile Ile Leu Pro Val Gly Ala Val Ala Leu Ile Val
        195                 200                 205

Ala Leu Phe Met Val Val Phe Leu Ile Pro Gly Gly Lys Glu Phe Leu
210                 215                 220

Tyr His His Met Gly Val Asp Thr Tyr Gln Ile Asn Arg Leu Ser Ala
225                 230                 235                 240

Trp Leu Asn Pro Phe Asp Tyr Ala Gly Ser Ile Ala Tyr Gln Gln Thr
                245                 250                 255

Gln Gly Met Ile Ser Ile Gly Ser Gly Leu Phe Gly Lys Gly Phe
            260                 265                 270

Asn Ile Val Glu Leu Pro Val Pro Val Arg Glu Ser Asp Met Ile Phe
        275                 280                 285

Thr Val Ile Ala Glu Asn Phe Gly Phe Ile Gly Gly Ser Ile Val Leu
        290                 295                 300

Ala Leu Tyr Leu Ile Leu Ile Tyr Arg Met Leu Arg Val Thr Phe Ala
305                 310                 315                 320

Ser Asn Asn Leu Phe Tyr Thr Tyr Ile Ser Thr Gly Phe Ile Met Met
                325                 330                 335

Ile Leu Phe His Ile Phe Glu Asn Ile Gly Ala Ala Val Gly Ile Leu
            340                 345                 350
```

```
Pro Leu Thr Gly Ile Pro Leu Pro Phe Ile Ser Gln Gly Gly Ser Ser
        355                 360                 365

Leu Ile Ser Asn Leu Ile Gly Val Gly Leu Val Leu Ser Met Ser Tyr
    370                 375                 380

Gln Asn Ser Leu Asn Gln Glu Lys Ala Thr Glu Arg Tyr Phe Ala His
385                 390                 395                 400

Ile Lys Lys Glu Ser Leu Thr Ser
                405

<210> SEQ ID NO 4
<211> LENGTH: 416
<212> TYPE: PRT
<213> ORGANISM: Streptococcus pneumoniae

<400> SEQUENCE: 4

Leu Tyr Glu Ser Ile Arg Leu Val Tyr Met Lys Arg Ser Leu Asp Ser
1               5                   10                  15

Arg Val Asp Tyr Ser Leu Leu Pro Val Phe Phe Leu Leu Val Ile
            20                  25                  30

Gly Val Val Ala Ile Tyr Ile Ala Val Ser His Asp Tyr Pro Asn Asn
        35                  40                  45

Ile Leu Pro Ile Leu Gly Gln Gln Val Ala Trp Ile Ala Leu Gly Leu
    50                  55                  60

Val Ile Gly Phe Val Val Met Leu Phe Asn Thr Glu Phe Leu Trp Lys
65                  70                  75                  80

Val Thr Pro Phe Leu Tyr Ile Leu Gly Leu Gly Leu Met Ile Leu Pro
                85                  90                  95

Ile Val Phe Tyr Asn Pro Ser Leu Val Ala Ser Thr Gly Ala Lys Asn
                100                 105                 110

Trp Val Ser Ile Asn Gly Ile Thr Leu Phe Gln Pro Ser Glu Phe Met
            115                 120                 125

Lys Ile Ser Tyr Ile Leu Met Leu Ala Arg Val Ile Val Gln Phe Thr
130                 135                 140

Lys Lys His Lys Glu Trp Arg Arg Thr Val Pro Leu Asp Phe Leu Leu
145                 150                 155                 160

Ile Phe Trp Met Ile Leu Phe Thr Ile Pro Val Leu Val Leu Leu Ala
                165                 170                 175

Leu Gln Ser Asp Leu Gly Thr Ala Leu Val Phe Val Ala Ile Phe Ser
            180                 185                 190

Gly Ile Val Leu Leu Ser Gly Val Ser Trp Lys Ile Ile Pro Val
        195                 200                 205

Phe Val Thr Ala Val Thr Gly Val Ala Gly Phe Leu Ala Ile Phe Ile
    210                 215                 220

Ser Lys Asp Gly Arg Ala Phe Leu His Gln Ile Gly Met Pro Thr Tyr
225                 230                 235                 240

Gln Ile Asn Arg Ile Leu Ala Trp Leu Asn Pro Phe Glu Phe Ala Gln
                245                 250                 255

Thr Thr Thr Tyr Gln Gln Ala Gln Gly Gln Ile Ala Ile Gly Ser Gly
            260                 265                 270

Gly Leu Phe Gly Gln Gly Phe Asn Ala Ser Asn Leu Leu Ile Pro Val
        275                 280                 285

Arg Glu Ser Asp Met Ile Phe Thr Val Ile Ala Glu Asp Phe Gly Phe
    290                 295                 300

Ile Gly Ser Val Leu Val Ile Ala Leu Tyr Leu Met Leu Ile Tyr Arg
```

```
               305                 310                 315                 320
Met Leu Lys Ile Thr Leu Lys Ser Asn Asn Gln Phe Tyr Thr Tyr Ile
                325                 330                 335

Ser Thr Gly Leu Ile Met Met Leu Leu Phe His Ile Phe Glu Asn Ile
                340                 345                 350

Gly Ala Val Thr Gly Leu Leu Pro Leu Thr Gly Ile Pro Leu Pro Phe
                355                 360                 365

Ile Ser Gln Gly Gly Ser Ala Ile Ile Ser Asn Leu Ile Gly Val Gly
            370                 375                 380

Leu Leu Leu Ser Met Ser Tyr Gln Thr Asn Leu Ala Glu Glu Lys Ser
385                 390                 395                 400

Gly Lys Val Pro Phe Lys Arg Lys Lys Val Val Leu Lys Gln Ile Lys
                405                 410                 415

<210> SEQ ID NO 5
<211> LENGTH: 395
<212> TYPE: PRT
<213> ORGANISM: Enterococcus faecalis

<400> SEQUENCE: 5

Met Asn Arg Lys Glu Lys Thr Asn Leu Asp Ser Arg Ile Asp Tyr Gly
1               5                  10                  15

Val Ile Leu Pro Val Phe Leu Leu Ser Leu Ile Gly Met Leu Ser Leu
                20                  25                  30

Tyr Val Ala Leu Tyr Asn Asp Pro Ser Lys Pro Lys Ile Gly Ser Leu
            35                  40                  45

Leu Met Lys Gln Gly Leu Trp Tyr Leu Val Gly Gly Leu Ser Ile Val
50                  55                  60

Ile Ile Met His Phe Ser Ser Lys Leu Leu Trp Arg Leu Thr Pro Val
65                  70                  75                  80

Phe Tyr Ala Leu Gly Leu Val Leu Met Gly Leu Leu Lys Phe Tyr
                85                  90                  95

Asp Pro Val Leu Ala Glu Gln Thr Gly Ser Lys Asn Trp Ile Arg Phe
                100                 105                 110

Gly Gly Thr Thr Phe Gln Pro Ser Glu Leu Met Lys Ile Ala Phe Ile
            115                 120                 125

Leu Met Leu Ala Tyr Ile Val Thr Met His Asn Val Lys Tyr Val Asp
            130                 135                 140

Arg Thr Leu Lys Ser Asp Phe Trp Leu Ile Ala Lys Met Leu Leu Val
145                 150                 155                 160

Ala Ile Pro Val Ile Val Leu Leu Gln Lys Asp Phe Gly Thr
                165                 170                 175

Met Leu Val Phe Leu Ala Ile Phe Gly Gly Val Phe Leu Met Ser Gly
                180                 185                 190

Ile Thr Trp Lys Ile Ile Val Pro Val Phe Ile Leu Ala Ala Leu Val
            195                 200                 205

Gly Ala Gly Thr Ile Tyr Leu Ile Thr Thr Glu Thr Gly Arg Asp Leu
        210                 215                 220

Leu Ser Lys Leu Gly Val Glu Ala Tyr Lys Phe Asp Arg Ile Asp Leu
225                 230                 235                 240

Trp Leu Asn Pro Phe His Thr Asp Pro Asp Arg Ser Phe Gln Pro Ala
                245                 250                 255

Leu Ala Leu Thr Ala Ile Gly Ser Gly Gly Leu Phe Gly Lys Gly Phe
                260                 265                 270
```

-continued

Asn Val Ser Asp Val Tyr Val Pro Val Arg Glu Ser Asp Met Ile Phe
            275                 280                 285

Thr Val Val Gly Glu Asn Phe Gly Phe Ile Gly Gly Cys Phe Ile Ile
        290                 295                 300

Leu Leu Tyr Phe Ile Leu Ile Tyr Arg Met Ile Arg Val Cys Phe Asp
305                 310                 315                 320

Thr Asn Asn Glu Phe Tyr Ala Tyr Ile Ala Thr Gly Ile Ile Met Met
                325                 330                 335

Ile Leu Phe His Val Phe Glu Asn Ile Gly Ala Asn Ile Gly Leu Leu
            340                 345                 350

Pro Leu Thr Gly Ile Pro Leu Pro Phe Ile Ser Gln Gly Gly Ser Ser
        355                 360                 365

Ile Leu Gly Asn Met Ile Gly Val Gly Leu Ile Met Ser Met Arg Tyr
370                 375                 380

Gln Gln Glu Thr Val Arg Thr Arg Ser Gly Arg
385                 390                 395

<210> SEQ ID NO 6
<211> LENGTH: 434
<212> TYPE: PRT
<213> ORGANISM: Streptococcus pyogenes

<400> SEQUENCE: 6

Met Ile Ile Ser Arg Ser Arg Gly Lys Thr Met Lys Ile Asp Lys Arg
1               5                   10                  15

His Leu Leu Asn Tyr Ser Ile Leu Leu Pro Tyr Leu Ile Leu Ser Val
            20                  25                  30

Ile Gly Leu Ile Met Val Tyr Ser Thr Thr Ser Val Ser Leu Ile Gln
        35                  40                  45

Ala His Ala Asn Pro Phe Lys Ser Val Ile Asn Gln Gly Val Phe Trp
    50                  55                  60

Ile Ile Ser Leu Val Ala Ile Thr Phe Ile Tyr Lys Leu Lys Leu Asn
65                  70                  75                  80

Phe Leu Thr Asn Thr Arg Val Leu Thr Val Met Leu Gly Glu Ala
            85                  90                  95

Phe Leu Leu Ile Ile Ala Arg Phe Phe Thr Thr Ala Ile Lys Gly Ala
            100                 105                 110

His Gly Trp Ile Val Ile Gly Pro Val Ser Phe Gln Pro Ala Glu Tyr
        115                 120                 125

Leu Lys Ile Ile Met Val Trp Tyr Leu Ala Leu Thr Phe Ala Lys Ile
    130                 135                 140

Gln Lys Asn Ile Ser Leu Tyr Asp Tyr Gln Ala Leu Thr Arg Arg Lys
145                 150                 155                 160

Trp Trp Pro Thr Gln Trp Asn Asp Leu Arg Asp Trp Arg Val Tyr Ser
                165                 170                 175

Leu Leu Met Val Leu Leu Val Ala Ala Gln Pro Asp Leu Gly Asn Ala
            180                 185                 190

Ser Ile Ile Val Leu Thr Ala Ile Ile Met Phe Ser Ile Ser Gly Ile
        195                 200                 205

Gly Tyr Arg Trp Phe Ser Ala Ile Leu Val Met Ile Thr Gly Leu Ser
    210                 215                 220

Thr Val Phe Leu Gly Thr Ile Ala Val Ile Gly Val Glu Arg Val Ala
225                 230                 235                 240

Lys Ile Pro Val Phe Gly Tyr Val Ala Lys Arg Phe Ser Ala Phe Phe
                245                 250                 255

```
Asn Pro Phe His Asp Leu Thr Asp Ser Gly His Gln Leu Ala Asn Ser
            260                 265                 270
Tyr Tyr Ala Met Ser Asn Gly Gly Trp Phe Gly Gln Gly Leu Gly Asn
            275                 280                 285
Ser Ile Glu Lys Arg Gly Tyr Leu Pro Glu Ala Gln Thr Asp Phe Val
    290                 295                 300
Phe Ser Val Val Ile Glu Glu Leu Gly Leu Ile Gly Ala Gly Phe Ile
305                 310                 315                 320
Leu Ala Leu Val Phe Phe Leu Ile Leu Arg Ile Met Asn Val Gly Ile
                325                 330                 335
Lys Ala Lys Asn Pro Phe Asn Ala Met Met Ala Leu Gly Val Gly Gly
            340                 345                 350
Met Met Leu Met Gln Val Phe Val Asn Ile Gly Ile Ser Gly Leu
                355                 360                 365
Ile Pro Ser Thr Gly Val Thr Phe Pro Phe Leu Ser Gln Gly Gly Asn
    370                 375                 380
Ser Leu Leu Val Leu Ser Val Ala Val Gly Phe Val Leu Asn Ile Asp
385                 390                 395                 400
Ala Ser Glu Lys Arg Asp Asp Ile Phe Lys Glu Ala Glu Leu Ser Tyr
                405                 410                 415
Arg Lys Asp Thr Arg Lys Glu Asn Ser Lys Val Val Asn Ile Lys Gln
                420                 425                 430
Phe Gln

<210> SEQ ID NO 7
<211> LENGTH: 528
<212> TYPE: PRT
<213> ORGANISM: Streptococcus pyogenes

<400> SEQUENCE: 7

Leu Lys Gln Glu Thr Tyr Met Lys Lys Leu Ile Leu Ser Cys Leu Val
1               5                   10                  15
Ala Leu Ala Leu Leu Phe Gly Gly Met Ser Arg Ala Gln Ala Asn Gln
                20                  25                  30
Tyr Leu Arg Val Gly Met Glu Ala Ala Tyr Ala Pro Phe Asn Trp Thr
            35                  40                  45
Gln Asp Asp Ala Ser Asn Gly Ala Val Pro Ile Glu Gly Thr Ser Gln
    50                  55                  60
Tyr Ala Asn Gly Tyr Asp Val Gln Val Ala Lys Lys Val Ala Lys Ala
65                  70                  75                  80
Met Asn Lys Glu Leu Leu Val Val Lys Thr Ser Trp Thr Gly Leu Ile
                85                  90                  95
Pro Ala Leu Thr Ser Gly Lys Ile Asp Met Ile Ala Ala Gly Met Ser
            100                 105                 110
Pro Thr Lys Glu Arg Arg Asn Glu Ile Ser Phe Ser Asn Ser Ser Tyr
        115                 120                 125
Thr Ser Gln Pro Val Leu Val Val Thr Ala Asn Gly Lys Tyr Ala Asp
    130                 135                 140
Ala Thr Ser Leu Lys Asp Phe Ser Gly Ala Lys Val Thr Ala Gln Gln
145                 150                 155                 160
Gly Val Trp His Val Asn Leu Leu Thr Gln Leu Lys Gly Ala Lys Leu
                165                 170                 175
Gln Thr Pro Met Gly Asp Phe Ser Gln Met Arg Gln Ala Leu Thr Ser
            180                 185                 190
```

```
Gly Val Ile Asp Ala Tyr Ile Ser Glu Arg Pro Glu Ala Met Thr Ala
            195                 200                 205

Glu Ala Ala Asp Ser Arg Leu Lys Met Ile Thr Leu Lys Lys Gly Phe
            210                 215                 220

Ala Val Ala Glu Ser Asp Ala Ala Ile Ala Val Gly Met Lys Lys Asn
225                 230                 235                 240

Asp Asp Arg Met Ala Thr Val Asn Gln Val Leu Glu Gly Phe Ser Gln
                245                 250                 255

Thr Asp Arg Met Ala Leu Met Asp Asp Met Val Thr Lys Gln Pro Val
            260                 265                 270

Glu Lys Lys Ala Glu Asp Ala Lys Ala Ser Phe Leu Gly Gln Met Trp
            275                 280                 285

Ala Ile Phe Lys Gly Asn Trp Lys Gln Phe Leu Arg Gly Thr Gly Met
            290                 295                 300

Thr Leu Leu Ile Ser Met Val Gly Thr Ile Thr Gly Leu Phe Ile Gly
305                 310                 315                 320

Leu Leu Ile Gly Ile Phe Arg Thr Ala Pro Lys Ala Lys His Lys Val
                325                 330                 335

Ala Ala Leu Gly Gln Lys Leu Phe Gly Trp Leu Leu Thr Ile Tyr Ile
            340                 345                 350

Glu Ile Phe Arg Gly Thr Pro Met Ile Val Gln Ser Met Val Ile Tyr
            355                 360                 365

Tyr Gly Thr Ala Gln Ala Phe Gly Ile Ser Ile Asp Arg Thr Leu Ala
            370                 375                 380

Ala Ile Phe Ile Val Ser Ile Asn Thr Gly Ala Tyr Met Ser Glu Ile
385                 390                 395                 400

Val Arg Gly Gly Ile Phe Ala Val Asp Lys Gly Gln Phe Lys Ala Ala
                405                 410                 415

Thr Ala Leu Gly Phe Thr His Gly Gln Thr Met Arg Lys Ile Val Leu
            420                 425                 430

Pro Gln Val Val Arg Asn Ile Leu Pro Ala Thr Gly Asn Glu Phe Val
            435                 440                 445

Ile Asn Ile Lys Asp Thr Ser Val Leu Asn Val Ile Ser Val Val Glu
450                 455                 460

Leu Tyr Phe Ser Gly Asn Thr Val Ala Thr Gln Thr Tyr Gln Tyr Phe
465                 470                 475                 480

Gln Thr Phe Thr Ile Ile Ala Ile Ile Tyr Phe Val Leu Thr Phe Thr
                485                 490                 495

Val Thr Arg Ile Leu Arg Tyr Ile Glu Arg Arg Phe Asp Ala Asp Thr
            500                 505                 510

Tyr Thr Thr Gly Ala Asn Gln Met Gln Ile Ala Glu Val Ser Asn Val
            515                 520                 525

<210> SEQ ID NO 8
<211> LENGTH: 521
<212> TYPE: PRT
<213> ORGANISM: Streptococcus pneumoniae

<400> SEQUENCE: 8

Met Arg Lys Ile Tyr Leu Ser Ile Phe Thr Ser Leu Leu Leu Met Leu
1               5                   10                  15

Gly Leu Val Asn Val Ala Gln Ala Asp Glu Tyr Leu Arg Ile Gly Met
            20                  25                  30

Glu Ala Ala Tyr Ala Pro Phe Asn Trp Thr Gln Asp Asp Asp Ser Asn
```

-continued

```
                 35                  40                  45
Gly Ala Val Lys Ile Asp Gly Thr Asn Gln Tyr Ala Asn Gly Tyr Asp
 50                  55                  60
Val Gln Ile Ala Lys Lys Ile Ala Lys Asp Leu Gly Lys Glu Pro Leu
 65                  70                  75                  80
Val Val Lys Thr Lys Trp Glu Gly Leu Val Pro Ala Leu Thr Ser Gly
                 85                  90                  95
Lys Ile Asp Met Ile Ile Ala Gly Met Ser Pro Thr Ala Glu Arg Lys
                100                 105                 110
Gln Glu Ile Ala Phe Ser Ser Tyr Tyr Thr Ser Glu Pro Val Leu
        115                 120                 125
Leu Val Lys Lys Asp Ser Ala Tyr Ala Ser Ala Lys Ser Leu Asp Asp
        130                 135                 140
Phe Asn Gly Ala Lys Ile Thr Ser Gln Gln Gly Val Tyr Leu Tyr Asn
145                 150                 155                 160
Leu Ile Ala Gln Ile Pro Gly Ala Lys Lys Glu Thr Ala Met Gly Asp
                165                 170                 175
Phe Ala Gln Met Arg Gln Ala Leu Glu Ala Gly Val Ile Asp Ala Tyr
                180                 185                 190
Val Ser Glu Arg Pro Glu Ala Leu Thr Ala Glu Ala Asn Ser Lys
        195                 200                 205
Phe Lys Met Ile Gln Val Glu Pro Gly Phe Lys Thr Gly Glu Glu Asp
        210                 215                 220
Thr Ala Ile Ala Ile Gly Leu Arg Lys Asn Asp Asn Arg Ile Ser Gln
225                 230                 235                 240
Ile Asn Ala Ser Ile Glu Thr Ile Ser Lys Asp Asp Gln Val Ala Leu
                245                 250                 255
Met Asp Arg Met Ile Lys Glu Gln Pro Ala Glu Ala Thr Thr Thr Glu
                260                 265                 270
Glu Thr Ser Ser Ser Phe Phe Ser Gln Val Ala Lys Ile Leu Ser Glu
        275                 280                 285
Asn Trp Gln Gln Leu Leu Arg Gly Ala Gly Ile Thr Leu Leu Ile Ser
        290                 295                 300
Ile Val Gly Thr Ile Ile Gly Leu Ile Ile Gly Leu Ala Ile Gly Val
305                 310                 315                 320
Phe Arg Thr Ala Pro Leu Ser Glu Asn Lys Val Ile Tyr Gly Leu Gln
                325                 330                 335
Lys Leu Val Gly Trp Val Leu Asn Val Tyr Ile Glu Ile Phe Arg Gly
                340                 345                 350
Thr Pro Met Ile Val Gln Ser Met Val Ile Tyr Tyr Gly Thr Ala Gln
                355                 360                 365
Ala Phe Gly Ile Asn Leu Asp Arg Thr Leu Ala Ala Ile Phe Ile Val
        370                 375                 380
Ser Ile Asn Thr Gly Ala Tyr Met Thr Glu Ile Val Arg Gly Gly Ile
385                 390                 395                 400
Leu Ala Val Asp Lys Gly Gln Phe Glu Ala Ala Thr Ala Leu Gly Met
                405                 410                 415
Thr His Asn Gln Thr Met Arg Lys Ile Val Leu Pro Gln Val Val Arg
        420                 425                 430
Asn Ile Leu Pro Ala Thr Gly Asn Glu Phe Val Ile Asn Ile Lys Asp
        435                 440                 445
Thr Ser Val Leu Asn Val Ile Ser Val Val Glu Leu Tyr Phe Ser Gly
450                 455                 460
```

-continued

Asn Thr Val Ala Thr Gln Thr Tyr Gln Tyr Phe Gln Thr Phe Thr Ile
465                 470                 475                 480

Ile Ala Val Ile Tyr Phe Val Leu Thr Phe Thr Val Thr Arg Ile Leu
            485                 490                 495

Arg Phe Ile Glu Arg Arg Met Asp Met Asp Thr Tyr Thr Thr Gly Ala
            500                 505                 510

Asn Gln Met Gln Thr Glu Asp Leu Lys
        515                 520

<210> SEQ ID NO 9
<211> LENGTH: 517
<212> TYPE: PRT
<213> ORGANISM: Streptococcus mutans

<400> SEQUENCE: 9

Met Lys Lys Thr Ile Leu Ser Cys Leu Ala Leu Phe Met Leu Phe
1               5                   10                  15

Ile Gly Val Thr Asn Ala Gln Ala Asp Asn Tyr Leu Arg Val Gly Met
            20                  25                  30

Glu Ala Ala Tyr Ala Pro Phe Asn Trp Thr Gln Asp Asn Ser Ser Asn
        35                  40                  45

Gly Ala Val Pro Ile Glu Gly Thr Lys Gln Tyr Ala Asn Gly Tyr Asp
    50                  55                  60

Val Gln Thr Ala Lys Lys Ile Ala Lys Thr Leu Gly Lys Lys Pro Leu
65                  70                  75                  80

Ile Val Lys Thr Lys Trp Glu Gly Leu Val Pro Ala Leu Thr Ser Gly
                85                  90                  95

Lys Ile Asp Leu Ile Ile Ala Gly Met Ser Pro Thr Lys Glu Arg Lys
            100                 105                 110

Lys Glu Ile Ala Phe Ser Asn Ser Tyr Tyr Thr Ser Glu Pro Val Leu
        115                 120                 125

Val Val Arg Lys Asp Ser Lys Tyr Ala Lys Ala Lys Asn Leu Asn Asp
    130                 135                 140

Phe Ser Gly Ala Lys Val Thr Ser Gln Gln Gly Val Tyr Leu Tyr Asn
145                 150                 155                 160

Leu Ile Asn Gln Ile Pro Lys Val Ser Arg Gln Thr Ala Met Gly Asp
                165                 170                 175

Phe Ser Gln Met Arg Gln Ala Leu Ala Ser Asn Val Ile Asp Ala Tyr
            180                 185                 190

Val Ser Glu Arg Pro Glu Ala Leu Ser Ser Thr Lys Ala Asn Ser Asn
        195                 200                 205

Phe Lys Met Val Ser Leu Lys Asn Gly Phe Lys Val Ser Lys Ser Asp
    210                 215                 220

Val Thr Ile Ala Val Gly Met Arg Lys Gly Asp Pro Arg Ile Glu Gln
225                 230                 235                 240

Val Asn Ala Ala Leu Asp Gln Phe Pro Leu Lys Glu Gln Ile Ser Leu
                245                 250                 255

Met Asp Lys Ile Ile Pro Met Gln Pro Ser Gln Asn Asn Ser Asp Gln
            260                 265                 270

Lys Glu Ser Lys Ser Asn Phe Phe Asp Gln Val Ser Lys Ile Val Lys
        275                 280                 285

Asn Asn Trp Lys Ala Leu Leu Arg Gly Thr Gly Val Thr Leu Leu Ile
    290                 295                 300

Ser Ile Ile Gly Thr Ile Ala Gly Leu Ile Ile Gly Leu Leu Ile Gly

```
                              305                 310                 315                 320
Val Tyr Arg Thr Ala Pro Lys Ala Ser Asn Leu Ile Leu Ala Trp Leu
                325                 330                 335

Gln Lys Ile Phe Gly Trp Leu Leu Thr Val Tyr Ile Glu Val Phe Arg
                340                 345                 350

Gly Thr Pro Met Ile Val Gln Ala Met Val Ile Tyr Tyr Gly Thr Ala
                355                 360                 365

Gln Ala Phe Gly Val Ser Leu Asp Arg Thr Leu Ala Ala Ile Phe Ile
                370                 375                 380

Val Ser Ile Asn Thr Gly Ala Tyr Met Ser Glu Ile Val Arg Gly Gly
385                 390                 395                 400

Ile Phe Ala Val Asp Lys Gly Gln Phe Glu Ala Ala Thr Ala Leu Gly
                405                 410                 415

Phe Thr His Arg Gln Thr Met Arg Lys Ile Val Leu Pro Gln Val Val
                420                 425                 430

Arg Asn Ile Leu Pro Ala Thr Gly Asn Glu Phe Val Ile Asn Ile Lys
                435                 440                 445

Asp Thr Ser Val Leu Asn Val Ile Ser Val Val Glu Leu Tyr Phe Ser
450                 455                 460

Gly Asn Thr Val Ala Thr Gln Thr Tyr Gln Tyr Phe Gln Thr Phe Phe
465                 470                 475                 480

Ile Ile Ala Val Ile Tyr Phe Ile Leu Thr Phe Thr Val Thr Arg Ile
                485                 490                 495

Leu Arg Leu Val Glu Arg Lys Met Asp Gln Asp Asn Tyr Thr Lys Ile
                500                 505                 510

Glu Gly Glu Thr Asn
        515

<210> SEQ ID NO 10
<211> LENGTH: 547
<212> TYPE: PRT
<213> ORGANISM: Enterococcus faecalis

<400> SEQUENCE: 10

Leu Leu Ile Glu Lys Arg Gln Asn Asp Gln Ser Asp Lys Lys Phe Lys
1               5                   10                  15

Gly Glu Lys Lys Met Asn Lys Lys Val Phe Ser Phe Ser Leu Leu Leu
                20                  25                  30

Val Thr Leu Phe Ser Leu Leu Gly Met Thr Thr Asn Ala Ser Ala Glu
                35                  40                  45

Glu Asn Gly Glu Phe Arg Val Gly Met Glu Ala Gly Tyr Ala Pro Phe
                50                  55                  60

Asn Trp Ser Gln Lys Asn Asp Ala His Gly Ala Val Pro Ile Gln Gly
65                  70                  75                  80

Asn Ser Tyr Ala Gly Gly Tyr Asp Val Gln Ile Ser Lys Lys Ile Ala
                85                  90                  95

Asp Gly Leu Gly Arg Lys Leu Val Ile Val Gln Thr Lys Trp Asp Gly
                100                 105                 110

Leu Ala Pro Ala Leu Gln Ser Gly Lys Ile Asp Ala Ile Ile Ala Gly
                115                 120                 125

Met Ser Pro Thr Ala Glu Arg Lys Lys Glu Ile Ala Phe Thr Asn Pro
                130                 135                 140

Tyr Tyr Glu Ser Gln Phe Val Val Ile Val Lys Lys Asp Gly Lys Tyr
145                 150                 155                 160
```

```
Ala Asn Ala Lys Ser Leu Lys Asp Leu Ala Asp Ala Lys Ile Thr Ala
            165                 170                 175
Gln Leu Asn Thr Phe His Tyr Gly Leu Ile Asp Gln Ile Pro Asn Val
        180                 185                 190
Asn Lys Gln Gln Ala Met Asp Asn Phe Ser Ala Met Arg Thr Ala Leu
    195                 200                 205
Ala Ser Gly Met Ile Asp Gly Tyr Val Ser Glu Arg Pro Glu Gly Ile
210                 215                 220
Thr Ala Thr Ser Val Asn Lys Glu Leu Lys Met Leu Glu Phe Pro Lys
225                 230                 235                 240
Glu Lys Gly Phe Asp Ala Ser Ala Glu Asp Ser Gln Val Ala Val Gly
            245                 250                 255
Met Arg Lys Gly Asp Pro Asp Ile Glu Lys Val Asn Lys Ile Leu Ala
        260                 265                 270
Gly Ile Ser Gln Asp Glu Arg Thr Lys Ile Met Asp Gln Ala Ile Lys
    275                 280                 285
Asp Gln Pro Ala Ala Thr Asp Ser Asp Glu Gln Lys Thr Gly Leu Ile
290                 295                 300
Asn Asp Phe Lys Asn Ile Trp Asn Gln Tyr Gly Asp Met Phe Leu Arg
305                 310                 315                 320
Gly Ala Gly Leu Thr Leu Phe Ile Ala Leu Ile Gly Thr Val Val Gly
            325                 330                 335
Thr Thr Leu Gly Leu Leu Ile Gly Val Phe Arg Thr Ile Pro Asp Ser
        340                 345                 350
Glu Asn Pro Val Ala Arg Phe Phe Gln Lys Leu Gly Asn Leu Ile Leu
    355                 360                 365
Ser Ile Tyr Ile Glu Val Phe Arg Gly Thr Pro Met Met Val Gln Ala
370                 375                 380
Met Val Ile Phe Tyr Gly Leu Ala Leu Ala Phe Gly Ile Ser Leu Asp
385                 390                 395                 400
Arg Thr Val Ala Ala Leu Phe Ile Val Ser Val Asn Thr Gly Ala Tyr
            405                 410                 415
Met Ser Glu Ile Val Arg Gly Gly Ile Phe Ala Val Asp Lys Gly Gln
        420                 425                 430
Phe Glu Ala Ala Gln Ala Ile Gly Met Thr His Gly Gln Thr Met Arg
    435                 440                 445
Lys Val Val Ile Pro Gln Val Leu Arg Asn Ile Leu Pro Ala Thr Gly
450                 455                 460
Asn Glu Phe Val Ile Asn Ile Lys Asp Thr Ala Val Leu Ser Val Ile
465                 470                 475                 480
Gly Val Ala Asp Leu Phe Phe Gln Gly Asn Ala Ala Ser Gly Ala Asn
            485                 490                 495
Phe Gln Phe Phe Gln Thr Phe Thr Ile Val Gly Ile Met Tyr Leu Val
        500                 505                 510
Met Thr Phe Val Ile Thr Arg Ile Leu Arg Val Val Glu Arg Lys Met
    515                 520                 525
Asp Gly Pro Ser Ala Tyr Val Lys Val Glu Glu Leu Thr Glu Glu Gly
530                 535                 540
Lys Glu Ser
545

<210> SEQ ID NO 11
<211> LENGTH: 485
<212> TYPE: PRT
```

<213> ORGANISM: Staphylococcus aureus

<400> SEQUENCE: 11

```
Met Lys Cys Leu Ile Arg Phe Ile Leu Val Leu Gly Leu Leu Ile Ser
1               5                   10                  15
Ser Ala Met Val Tyr Ile Asn Pro Thr Ala His Ala Glu Gln Asp Gln
            20                  25                  30
Thr Trp Glu Lys Ile Lys Glu Arg Gly Glu Leu Arg Val Gly Leu Ser
        35                  40                  45
Ala Asp Tyr Ala Pro Met Glu Phe Glu His Thr Val Asn Gly Lys Thr
    50                  55                  60
Glu Tyr Ala Gly Val Asp Ile Asp Leu Ala Lys Lys Ile Ala Lys Asp
65                  70                  75                  80
Asn Asn Leu Lys Leu Lys Ile Val Asn Met Ser Phe Asp Ser Leu Leu
                85                  90                  95
Gly Ala Leu Lys Thr Gly Lys Ile Asp Ile Ile Ile Ser Gly Met Thr
            100                 105                 110
Ser Thr Pro Glu Arg Lys Lys Gln Val Asp Phe Ser Asp Ser Tyr Met
        115                 120                 125
Met Thr Lys Asn Ile Met Leu Val Lys Lys Asp Lys Val Asn Glu Tyr
    130                 135                 140
Lys Asp Ile Lys Asp Phe Asn Asn Lys Val Gly Ala Gln Lys Gly
145                 150                 155                 160
Thr Glu Gln Glu Lys Ile Ala Gln Thr Glu Ile Glu Asn Ala Ser Ile
                165                 170                 175
Thr Ser Leu Ser Arg Leu Pro Asp Val Ile Leu Ala Leu Lys Ser Gly
            180                 185                 190
Lys Val Glu Gly Ala Val Val Glu Lys Pro Val Ala Glu Ala Tyr Leu
        195                 200                 205
Lys Gln Asn Pro Lys Leu Gly Ile Ser Asn Val Lys Phe Asn Glu Glu
    210                 215                 220
Glu Lys Asp Thr Val Ile Ala Val Pro Lys Asp Ser Pro Lys Leu Leu
225                 230                 235                 240
Ser Gln Ile Asn Lys Thr Ile Lys Glu Val Lys Asp Lys Gly Leu Ile
                245                 250                 255
Asp Lys Tyr Met Thr Asn Ala Ala Asn Ala Met Asn Asp Asp Ser Gly
            260                 265                 270
Phe Ile Ser Lys Tyr Gly Ser Phe Phe Leu Lys Gly Ile Lys Ile Thr
        275                 280                 285
Ile Leu Ile Ser Leu Ile Gly Val Ala Leu Gly Ser Ile Leu Gly Ala
    290                 295                 300
Phe Val Ala Leu Met Lys Leu Ser Lys Ile Lys Ile Ile Ser Trp Ile
305                 310                 315                 320
Ala Ser Ile Tyr Ile Glu Ile Leu Arg Gly Thr Pro Met Leu Val Gln
                325                 330                 335
Val Phe Ile Val Phe Phe Gly Ile Thr Ala Ala Leu Gly Leu Asp Ile
            340                 345                 350
Ser Ala Leu Val Cys Gly Thr Ile Ala Leu Val Ile Asn Ser Ser Ala
        355                 360                 365
Tyr Ile Ala Glu Ile Ile Arg Ala Gly Ile Asn Ala Val Asp Lys Gly
    370                 375                 380
Gln Met Glu Ala Ala Arg Ser Leu Gly Leu Asn Tyr Arg Gln Thr Met
385                 390                 395                 400
```

-continued

```
Lys Ser Val Ile Met Pro Gln Ala Ile Lys Asn Ile Leu Pro Ala Leu
                405                 410                 415

Gly Asn Glu Phe Val Thr Leu Ile Lys Glu Ser Ser Ile Val Ser Thr
                420                 425                 430

Ile Gly Val Gly Glu Ile Met Phe Asn Ala Gln Val Val Gln Gly Ile
                435                 440                 445

Ser Phe Asp Pro Phe Thr Pro Leu Ile Val Ala Ala Leu Tyr Phe
    450                 455                 460

Val Leu Thr Phe Val Leu Thr Arg Ile Met Asn Met Ile Glu Gly Arg
465                 470                 475                 480

Leu Asn Ala Ser Asp
                485

<210> SEQ ID NO 12
<211> LENGTH: 485
<212> TYPE: PRT
<213> ORGANISM: Staphylococcus epidermidis

<400> SEQUENCE: 12

Met Lys Cys Leu Phe Lys Met Leu Ser Ile Ile Ile Met Leu Ser
1               5                   10                  15

Thr Phe Thr Leu Phe Ile Ser Pro Ser Thr Tyr Ala Asn Glu Asp
                20                  25                  30

Asn Trp Thr Lys Ile Lys Asn Arg Gly Glu Leu Arg Val Gly Leu Ser
                35                  40                  45

Ala Asp Tyr Ala Pro Leu Glu Phe Glu Lys Thr Ile His Gly Lys Thr
    50                  55                  60

Glu Tyr Ala Gly Val Asp Ile Glu Leu Ala Lys Lys Ile Ala Lys Asp
65                  70                  75                  80

Asn His Leu Lys Leu Lys Ile Val Asn Met Gln Phe Asp Ser Leu Leu
                85                  90                  95

Gly Ala Leu Lys Thr Gly Lys Ile Asp Ile Ile Ile Ser Gly Met Thr
                100                 105                 110

Thr Thr Pro Glu Arg Lys Lys Glu Val Asp Phe Thr Lys Pro Tyr Met
                115                 120                 125

Ile Thr Asn Asn Val Met Met Ile Lys Lys Asp Asp Ala Lys Arg Tyr
    130                 135                 140

Gln Asn Ile Lys Asp Phe Glu Gly Lys Lys Ile Ala Ala Gln Lys Gly
145                 150                 155                 160

Thr Asp Gln Glu Lys Ile Ala Gln Thr Glu Ile Glu Asp Ser Lys Ile
                165                 170                 175

Ser Ser Leu Asn Arg Leu Pro Glu Ala Ile Leu Ser Leu Lys Ser Gly
                180                 185                 190

Lys Val Ala Gly Val Val Glu Lys Pro Val Gly Glu Ala Tyr Leu
                195                 200                 205

Lys Gln Asn Ser Glu Leu Thr Phe Ser Lys Ile Lys Phe Asn Glu Glu
    210                 215                 220

Lys Lys Gln Thr Cys Ile Ala Val Pro Lys Asn Ser Pro Val Leu Leu
225                 230                 235                 240

Asp Lys Leu Asn Gln Thr Ile Asp Asn Val Lys Glu Lys Asn Leu Ile
                245                 250                 255

Asp Gln Tyr Met Thr Lys Ala Ala Glu Asp Met Gln Asp Asp Gly Asn
                260                 265                 270

Phe Ile Ser Lys Tyr Gly Ser Phe Ile Lys Gly Ile Lys Asn Thr
    275                 280                 285
```

-continued

```
Ile Leu Ile Ser Leu Val Gly Val Leu Gly Ser Ile Leu Gly Ser
            290                 295                 300

Phe Ile Ala Leu Leu Lys Ile Ser Lys Ile Arg Pro Leu Gln Trp Ile
305                 310                 315                 320

Ala Ser Ile Tyr Ile Glu Phe Leu Arg Gly Thr Pro Met Leu Val Gln
                325                 330                 335

Val Phe Ile Val Phe Phe Gly Thr Thr Ala Ala Leu Gly Leu Asp Ile
            340                 345                 350

Ser Ala Leu Ile Cys Gly Thr Ile Ala Leu Val Ile Asn Ser Ser Ala
            355                 360                 365

Tyr Ile Ala Glu Ile Ile Arg Ala Gly Ile Asn Ala Val Asp Lys Gly
            370                 375                 380

Gln Thr Glu Ala Ala Arg Ser Leu Gly Leu Asn Tyr Arg Gln Thr Met
385                 390                 395                 400

Gln Ser Val Val Met Pro Gln Ala Ile Lys Lys Ile Leu Pro Ala Leu
                405                 410                 415

Gly Asn Glu Phe Val Thr Leu Ile Lys Glu Ser Ser Ile Val Ser Thr
            420                 425                 430

Ile Gly Val Ser Glu Ile Met Phe Asn Ala Gln Val Val Gln Gly Ile
            435                 440                 445

Ser Phe Asp Pro Phe Thr Pro Leu Leu Val Ala Ala Leu Leu Tyr Phe
            450                 455                 460

Leu Leu Thr Phe Ala Leu Thr Arg Val Met Asn Phe Ile Glu Gly Arg
465                 470                 475                 480

Met Ser Ala Ser Asp
                485

<210> SEQ ID NO 13
<211> LENGTH: 5
<212> TYPE: PRT
<213> ORGANISM: Staphylococcus aureus
<220> FEATURE:
<221> NAME/KEY: MISC_FEATURE
<222> LOCATION: (3)..(3)
<223> OTHER INFORMATION: X = Any amino acid

<400> SEQUENCE: 13

Leu Pro Xaa Thr Gly
1               5

<210> SEQ ID NO 14
<211> LENGTH: 22
<212> TYPE: PRT
<213> ORGANISM: Staphylococcus aureus

<400> SEQUENCE: 14

Ala Leu Lys Thr Gly Lys Ile Asp Ile Ile Ser Gly Met Thr Ser
1               5                   10                  15

Thr Pro Glu Arg Lys Lys
            20

<210> SEQ ID NO 15
<211> LENGTH: 18
<212> TYPE: PRT
<213> ORGANISM: Staphylococcus aureus

<400> SEQUENCE: 15

Val Glu Gly Ala Val Val Glu Lys Pro Val Ala Glu Ala Tyr Leu Lys
1               5                   10                  15
```

```
Gln Asn

<210> SEQ ID NO 16
<211> LENGTH: 15
<212> TYPE: PRT
<213> ORGANISM: Staphylococcus aureus

<400> SEQUENCE: 16

Glu Tyr Ala Gly Val Asp Ile Asp Leu Ala Lys Lys Ile Ala Lys
1               5                   10                  15
```

SURFACE PROTEINS FROM GRAM-POSITIVE BACTERIA HAVING HIGHLY CONSERVED MOTIFS AND ANTIBODIES THAT RECOGNIZE THEM

CROSS-REFERENCE TO RELATED APPLICATIONS

This application claims the benefit of U.S. Provisional Patent Application No. 60/289,132, filed May 8, 2001.

FIELD OF THE INVENTION

The present invention relates in general to surface-located proteins from gram-positive bacteria, and in particular to a group of proteins that contain highly conserved sequence motifs. In addition, the invention relates to polyclonal and monoclonal antibodies which can recognize these proteins and which can recognize the conserved motifs. Further, the invention relates to the use of the proteins, conserved motifs and antibodies generated thereto in compositions and methods used to treat or prevent infections and other pathogenic conditions caused by a wide-array of gram-positive bacteria.

BACKGROUND OF THE INVENTION

Bacterial surface proteins of gram-positive bacteria are known to be important during the infection process since they mediate bacterial attachment to host tissues, and/or interact with the host immune system. For example, in the gram-positive bacteria *Staphylococcus aureus*, several of these proteins have been well characterized and were found to bind extracellular matrix proteins such as collagen, fibronectin, fibrinogen, as well as immunoglobulin G. These binding proteins include fibronectin binding proteins such as disclosed in U.S. Pat. Nos. 5,175,096; 5,320,951; 5,416,021; 5,440,014; 5,571,514; 5,652,217; 5,707,702; 5,789,549; 5,840,846; 5,980,908; and 6,086,895; fibrinogen binding proteins such as disclosed in U.S. Pat. Nos. 6,008,341 and 6,177,084; and collagen binding proteins as disclosed in 5,851,794 and 6,288,214; all of these patents incorporated herein by reference.

Previous studies have shown that the collagen and fibronectin binding proteins have been shown to contribute to the virulence of *S. aureus* in animal models. In addition, immunization of mice with certain of these binding protein has been shown in some cases to provide protection from septic death due to *S. aureus*. However, in some cases, certain formulations based on bacterial proteins from specific gram-positive bacteria such as *S. aureus* were not always effective in treating patients, and moreover these formulations will generally be species specific and thus do not generally afford protection against infection from a variety of gram-positive bacteria. Accordingly, it is very important to develop ways of locating surface proteins which will be utilized effectively in methods of treating or preventing infection, and in particular it is highly desirable to develop methods of treatment which can be utilized in a broad-based application to treat or prevent a wide variety of infections caused by gram-positive bacteria.

SUMMARY OF THE INVENTION

Accordingly, it is an object of the present invention to provide methods for isolating proteins from gram-positive bacteria which can be utilized in methods of treating or preventing a wide range of infections caused by gram-positive bacteria.

It is another object of the present invention to provide surface proteins from gram-positive bacteria that have highly conserved sequence motifs near their carboxyl termini which can be utilized to generate antibodies that will be protective against a wide variety of gram positive bacteria.

It is further an object of the present invention to provide a method of generating an immune response to a wide variety of gram-positive bacteria by administering an immunogenic amount of an isolated peptide sequence which is highly conserved in gram positive bacteria or by administering proteins which include these highly conserved sequence motifs.

It is a further object of the present invention to provide a vaccine for treating or preventing infection from gram-positive bacteria which comprises an isolated peptide sequence which is highly conserved in gram positive bacteria or a protein which includes one or more of these highly conserved sequence motifs in an amount effective to generate an immune response to said peptides or proteins.

It is still further an object to provide compositions for treating or preventing an infection from gram-positive bacteria which comprise an isolated peptide sequence which is highly conserved in gram positive bacteria or a protein which includes one or more of these highly conserved sequence motifs and a pharmaceutically acceptable vehicle, carrier or excipient.

It is still further an object of the present invention to provide isolated antibodies which recognize these highly conserved sequence motifs or proteins which contain said motifs, and to utilize these antibodies in treating or preventing infection caused by a broad range of gram-positive bacteria.

It is an additional object of the present invention to provide diagnostic kits which can utilize the conserved sequences, proteins, and/or antibodies in accordance with the invention in order to diagnose and identify infections caused by gram-positive bacteria.

These and other objects are provided by virtue of the present invention which comprises the identification, isolation, and/or purification of highly conserved amino acid sequences from gram positive bacteria and proteins which contain said sequences, and the use of these sequences and/or proteins to treat or prevent infections caused by a wide range of gram-positive bacteria. In addition, the invention comprises monoclonal and polyclonal antibodies which recognize these sequences and proteins, as well as vaccines and other pharmaceutical compositions which utilize these peptide sequences and proteins, and methods of eliciting an immune response against a broad range of gram positive bacteria by administering the peptides and/or proteins to a human or animal in an amount effective to generate an immune response. The sequences and proteins of the present invention can thus be used in methods or achieving passive or active immunity in patients so as to treat or prevent a wide range of infections caused by gram-positive bacteria.

These embodiments and other alternatives and modifications within the spirit and scope of the disclosed invention are described in, or will become readily apparent from, reference to the detailed description of the preferred embodiments provided herein below.

BRIEF DESCRIPTION OF THE DRAWING FIGURES

Figure 1:
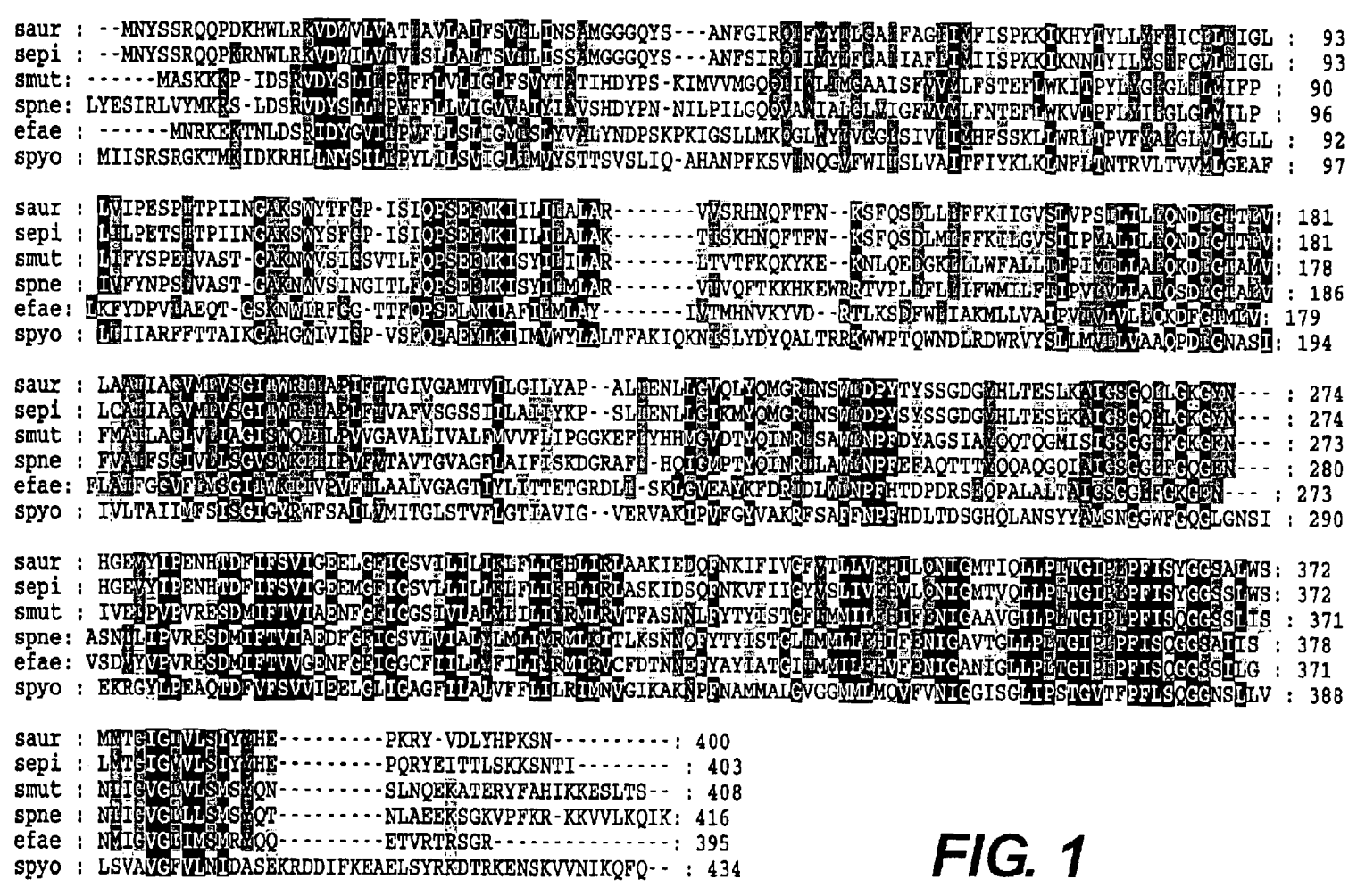

FIG. 1 is a depiction of ClustalW multiple sequence alignment of the amino acid sequences of the surface proteins in accordance with the invention which have been characterized as the cell division group (or group 1) from 6 Gram-positive bacteria, shown from top to bottom as saur, S. aureus; sepi, S. epidermidis; smut, S. mutans; spne, S. pneunomiae; efae; E. faecalis; and spyo, S. pyogenes, which are identified, respectively, as SEQ ID NOS 1–6. In the drawing figure, the dark-shaded regions represent highly conserved residues, and light-shaded regions represent relatively well-conserved residues.

Figure 2:
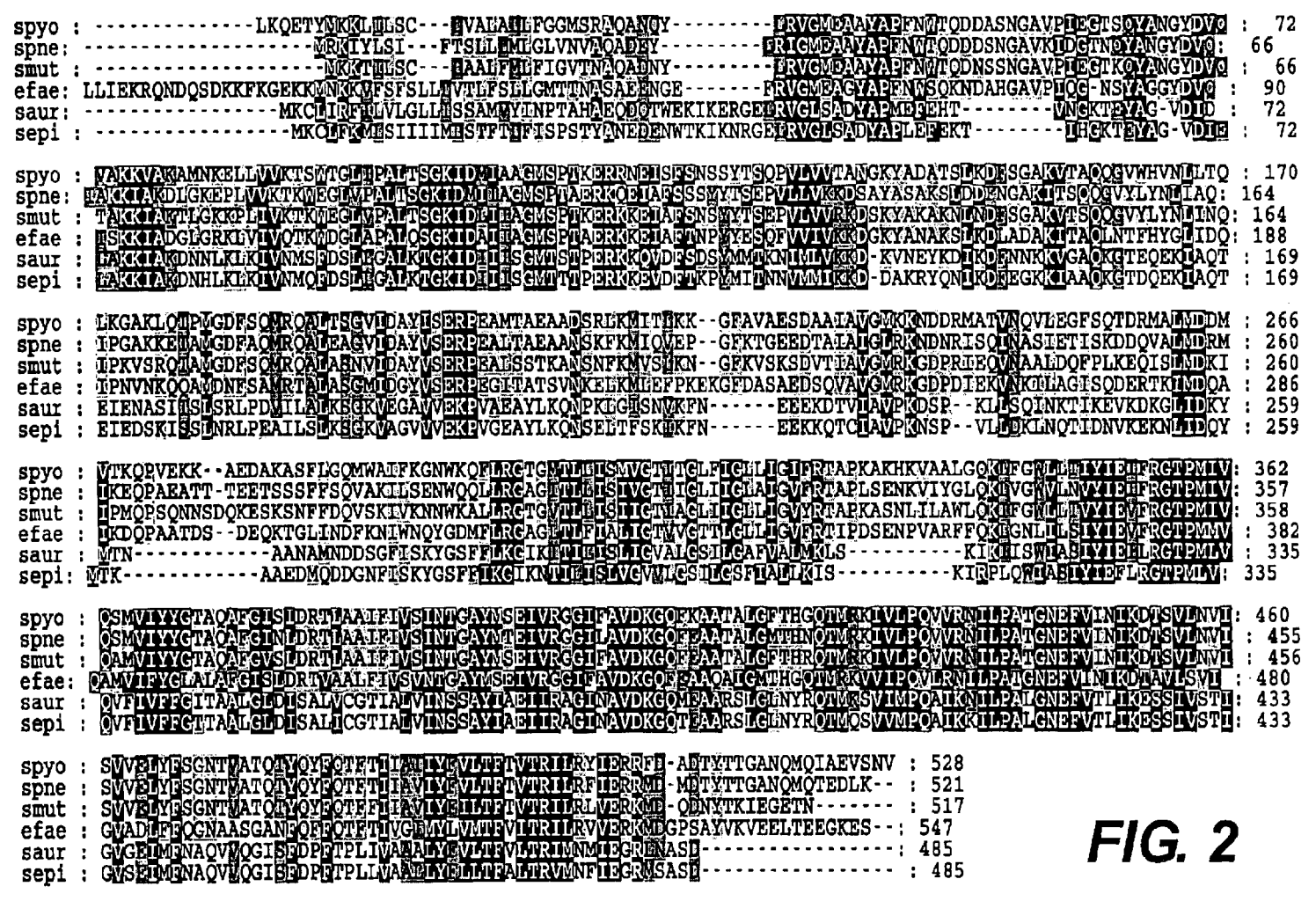

FIG. 2 is a depiction of ClustalW multiple sequence alignment of the amino acid sequences of the surface proteins in accordance with the invention which have been characterized as the amino acid transporter group (or group 2) from 6 Gram-positive bacteria, shown from top to bottom as spyo, S. pyogenes; spne, S. pneunomiae; smut, S. mutans; efae, E. faecalis; saur, S. aureus; and sepi, S. epidermidis; and which are identified, respectively, as SEQ ID NOS 7–12. In the drawing figure, the dark-shaded regions represent highly conserved residues, and light-shaded regions represent relatively well-conserved residues.

DETAILED DESCRIPTION OF THE PREFERRED EMBODIMENTS

In accordance with the present invention, the present inventors have isolated novel surfaces proteins from gram positive bacteria that are characterized in that they contain highly conserved sequences which can be utilized in the identification and isolation of surface proteins from gram positive bacteria, and which can be used to generate antibodies which will recognize said highly conserved sequences and/or the surface proteins containing said sequences. In particular, these novel proteins containing their unique highly conserved sequences were obtained in accordance with the invention using an algorithm the present inventors devised for reviewing publicly available sequence information regarding Gram-positive bacteria so as to identify and/or isolate and purify highly conserved regions in the genome and the proteins which contain those highly conserved regions. In the identification and isolation process of the invention, numerous genomes from Gram-positive bacteria are selected, and in a suitable example, genomes of six Gram-positive bacteria, namely *Staphylococcus aureus, Staphylococcus epidermidis, Enterococcus Faecalis, Streptococcus pyogenes, Streptococcus pneumoniae,* and *Streptococcus mutans,* all of which are important human pathogens, were selected and subject to the present identification process. The genomes of four *S. aureus* strains were publicly available at the time of the analysis and were all included in the process to identify conserved regions of the genome and/or proteome.

In the specific example, the *S. aureus* genome sequences were obtained from the websites of The Institute for Genomic Research (TIGR) (strain COL), The Sanger Center (a methicillin resistant strain and a methicillin sensitive strain), and University of Oklahoma's Advanced Center for Genome Technology (OU-ACGT) (strain 8325). The genome sequences of *E. faecalis* (strain V583), *S. epidermidis* (strain RP62A) and *S. pneumoniae* Type 4 were obtained from TIGR, and the sequences of *S. mutans* and *S. pyogenes* (group A) were from OU-ACGT.

In one preferred process, the identification steps or "data mining" was performed using a combination of software developed by the inventors, Glimmer2 from TIGR and stand-alone BLAST from the National Center for Biotechnology Information. The system was set up on a Silicon Graphics machine running IRIX6.5. In the preferred process of the present invention, an algorithm is used which consists of the following steps: (1) process each sequence file which usually contains multiple contigs into individual files each of which consists one contig; (2) predict genes based on the sequencing; (3) add a unique identification tag to each predicted gene so that genes from different organisms can be put into one single database; (4) extract genes from each genome; (5) translate each gene into its amino acid sequences; (6) form a blast searchable database of the protein sequences; and (7) perform a blast search of the database to find proteins that contain the desired conserved motif such as the LPXTG (SEQ ID NO: 13) motif wherein X can be any amino acid.

After LPXTG-containing proteins were identified, they were collected into a subset and used to establish a separate blast searchable database. Each protein in this subset was blasted against each other as well as to the large protein database to identify LPXTG-containing proteins that are conserved among these organisms. In the analysis of the LPXTG-containing proteins, two groups were located as discussed further below. Members in each group exhibited substantial overall sequence homology with each other as can be seen from Tables 1 and 2.

TABLE 1

Percentage amino acid sequence similarities among the cell division group (group 1) from 6 Gram-positive bacteria.

|  | E. faecalis | S. epidermidis | S. pneumoniae | S. pyogenes | S. mutans | S. aureus |
|---|---|---|---|---|---|---|
| E. faecalis | 100 | 55 | 66 | 41 | 67 | 56 |
| S. epidermidis |  | 100 | 52 | 41 | 53 | 90 |
| S. pneumoniae |  |  | 100 | 45 | 78 | 51 |
| S. pyogenes |  |  |  | 100 | 44 | 41 |
| S. mutans |  |  |  |  | 100 | 52 |
| S. aureus |  |  |  |  |  | 100 |

TABLE 2

Percentage amino acid sequence similarities among the amino acid transporter group (group 2) from 6 Gram-positive bacteria.

|  | S. pneumoniae | S. pyogenes | S. mutans | S. epidermidis | S. aureus | E. faecalis |
|---|---|---|---|---|---|---|
| S. pneumoniae | 100 | 81 | 91 | 51 | 51 | 69 |
| S. pyogenes |  | 100 | 81 | 48 | 48 | 68 |
| S. mutans |  |  | 100 | 51 | 51 | 67 |
| S. epidermidis |  |  |  | 100 | 87 | 49 |
| S. aureus |  |  |  |  | 100 | 49 |
| E. faecalis |  |  |  |  |  | 100 |

In addition, after multiple sequence alignment, there are stretches of completely identical sequences in each group, as shown in FIGS. 1 and 2. Moreover, a homology search with known genes indicated that the first group (SEQ ID NOS 1–6 of FIG. 1) appeared to be a novel group of proteins that belonged to a family of cell division proteins, while the second group (SEQ ID NOS 7–12 of FIG. 2) appeared to be characterized as a family of amino acid transporters. However, none of the proteins in the two groups has been described for the organisms that were analyzed, and therefore they are novel for these bacteria.

In addition, each protein in the two groups was examined for the presence of signal peptide through the SignalP mail server at Center for Biological Sequence Analysis, the Technical University of Denmark. Each was predicted to contain a signal peptide at the proper position, which appeared to confirm that these are surface proteins. In general, cell division proteins and amino acid transporters are important proteins for bacteria survival in vitro and in vivo. The fact that these proteins exhibit such high-level sequence conservation among the organisms suggests that they perform conserved functions, and it is clear that similar surface proteins are present in other Gram-positive bacteria which will also be characterized by the conserved regions in accordance with the present invention.

In addition to the sequence motif LPXTG which was discussed above, the present inventors uncovered 3 additional novel peptide sequences motifs that were conserved in the proteins identified using the method as described above. In particular, these conserved regions have the amino acid sequences identified as "SA-1": ALKTGKIDIIISGMTSTPERKK (SEQ ID NO:14); "SA-2": VEGAWEKPVAEAYLKQN (SEQ ID NO:15), and "SA-3": EYAGVDIDLAKKIAK (SEQ ID NO:16). The peptide sequences were selected from 3 regions in a *Staphylococcus aureus* protein that belongs to one ABC transporter group. Each region is highly conserved among the 6 Gram-positive bacteria examined (*Enterococcus faecalis, Staphylococcus epidernidis, Streptococcus pyogenes, Streptococcus mutans, Streptococcus pneumoniae*, and *Staphylococcus aureus*). Also, in order to increase the chance that the sequences will be exposed on the surface, we limited the selection of the sequences to hydrophilic regions using the method of Kyte and Doolittle.

In accordance with the present invention, these specific peptides may be obtained in any of a number of suitable ways well known in the art to generate peptides, and similarly, proteins containing these peptides may be obtained through physical isolation and/or separation methods from actual bacteria, or through conventional methods of protein synthesis. In the present case, one suitable method for preparing the peptides of the invention is through synthesis using an Advanced Chem Tech 396 multiple peptide synthesizer, using Fmoc chemistry and activation with HBTU. After cleavage from the resin, peptides can be purified by reverse-phase chromatography on a Waters Delta-Pak C18 column, eluted with gradient of acetonitrile in 0.1% trifluoroacetic acid/water. The purity of the peptides obtained in this fashion has been further confirmed by mass spectrometry analysis, and the peptide-KLH conjugation with EDC. The carrier protein KLH and the peptides (1:1 by weight) were coupled using EDC (Pierce) for 2 hours at room temperature. The reaction mixture is subjected to a desalting column pre-equilibrated with the purification buffer (0.083 M sodium phosphate, 0.9 M NaCl, pH 7.2). The conjugated peptides were eluted with the purification buffer and 0.5 ml fractions were collected. Each fraction was measured for its absorbance at 280 nm and the fractions containing the conjugate were pooled.

Accordingly, in accordance with the present invention, there are provided isolated amino acid sequences, namely ALKTGKIDIIISGMTSTPERKK (SEQ ID NO:14); VEGAWEKPVAEAYLKQN (SEQ ID NO:15), and EYAGVDIDLAKKIAK (SEQ ID NO:16), which are highly conserved regions in surface proteins from Gram-positive bacteria which can be utilized to generate antibodies that can recognize these sequences and which thus can be utilized in methods of treating or preventing a wide range of Gram-positive bacteria that will have proteins containing these sequences. In addition, it is contemplated that proteins from Gram-positive bacteria that contain these conserved sequences may also be isolated and/or purified, and may also be used to generate antibodies which recognize these proteins and which can be utilized in methods of treating or preventing infection caused by Gram-positive bacteria.

In accordance with the invention, the antibodies generated by immunization with either the conserved sequences described above or proteins containing these sequences may be either monoclonal or polyclonal, and may be prepared in any of a number of conventional ways well known to those of ordinary skill in the art. For example, monoclonal antibodies in accordance with the present invention may be produced, e.g., using the method of Kohler and Milstein (Nature 256:495–497, 1975), or other suitable ways known in the field, and in addition can be prepared as chimeric, humanized, or human monoclonal antibodies in ways that would be well known in this field. Still further, monoclonal antibodies may be prepared from a single chain, such as the light or heavy chains, and in addition may be prepared from active fragments of an antibody which retain the binding characteristics (e.g., specificity and/or affinity) of the whole antibody. By active fragments is meant an antibody fragment which has the same binding specificity as a complete antibody which recognizes and binds to the peptide sequences or the proteins of the present invention, and the term "antibody" as used herein is meant to include said fragments. Additionally, antisera prepared using monoclonal or polyclonal antibodies in accordance with the invention are also contemplated and may be prepared in a number of suitable ways as would be recognized by one skilled in the art.

As indicated above, antibodies which recognize the conserved sequences, or proteins containing these sequences, as set forth above, may be prepared in a number of suitable ways that would be well known in the art, such as the well-established Kohler and Milstein method described above which can be utilized to generate monoclonal antibodies. In one such method, mice are injected intraperitoneally once a week for a prolonged period with a antigen comprising a purified recombinant peptide or protein in accordance with the invention, followed by a test of blood obtained from the immunized mice to determine reactivity to the purified antigen. Following identification of mice suitably reactive to the antigen, lymphocytes isolated from mouse spleens may be fused to mouse myeloma cells to produce hybridomas positive for the antibodies against the peptides and/or proteins of the invention which are then isolated and cultured, following by purification and isotyping.

In order to generate monoclonal antibodies in accordance with the invention, it is thus preferred that these be generated using recombinantly prepared peptide sequences or proteins using conventional methods well known in the art. For example, one such method employs the use of *E. coli* expression vector pQE-30 as an expression vector for cloning and expressing recombinant proteins and peptides. In this method, PCR is used to amplify DNA coding for the peptide sequences of the invention, and a suitable *E. coli* expression vector such as PQE-30 (Qiagen) is used to allow for the expression of a recombinant fusion protein having the appropriate sequences. The cells containing these fusion proteins may be harvested, and the peptides of the invention may be eluted suing suitable buffer solutions. The peptides can then be subject to further purification steps, e.g., put through an endotoxin removal process, and the appropriate peptides obtained in this fashion may then be utilized to elicit an immune response and generate antibodies in accordance with the invention.

As indicated above, although production of antibodies using recombinant forms of the peptides or proteins of the invention is preferred, antibodies may be generated from natural isolated and purified proteins or peptides as well, and monoclonal or polyclonal antibodies can be generated using the natural peptides or proteins or active regions in the same manner as described above to obtain such antibodies. Still other conventional ways are available to generate the antibodies of the present invention using recombinant or natural purified peptides or proteins or its active regions, as would be recognized by one skilled in the art.

As would be recognized by one skilled in the art, the antibodies of the present invention may also be formed into suitable pharmaceutical compositions for administration to a human or animal patient in order to treat or prevent an infection caused by Gram-positive bacteria. Pharmaceutical compositions containing the antibodies of the present invention, or effective fragments thereof, may be formulated in combination with any suitable pharmaceutical vehicle, excipient or carrier that would commonly be used in this art, including such as saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art. Suitable methods of administration of any pharmaceutical composition disclosed in this application include, but are not limited to, topical, oral, anal, vaginal, intravenous, intraperitoneal, intramuscular, subcutaneous, intranasal and intradermal administration.

For topical administration, the composition is formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

Additional forms of antibody compositions, and other information concerning compositions, methods and applications with regard to other surface proteins will generally also be applicable to the present invention, including those antibodies and compositions as disclosed, for example, in U.S. Pat. No. 6,288,214 (Hook et al.), incorporated herein by reference. Similarly, other forms of antibody compositions, and other information concerning compositions, methods and applications with regard to other surface proteins and peptides which will also be applicable to the present invention are disclosed in U.S. Ser. No. 09/810,428, filed Mar. 19, 2001, incorporated herein by reference; and U.S. Ser. No. 09/386,962, filed Aug. 31, 1999, incorporated herein by reference.

The antibody compositions of the present invention may also be administered with a suitable adjuvant in an amount effective to enhance the immunogenic response against the conjugate. For example, suitable adjuvants may include alum (aluminum phosphate or aluminum hydroxide), which is used widely in humans, and other adjuvants such as saponin and its purified component Quil A, Freund's complete adjuvant, RIBBI adjuvant, and other adjuvants used in research and veterinary applications. Still other chemically defined preparations such as muramyl dipeptide, monophosphoryl lipid A, phospholipid conjugates such as those described by Goodman-Snitkoff et al. *J. Immunol.* 147:410–415 (1991) and incorporated by reference herein, encapsulation of the conjugate within a proteoliposome as described by Miller et al., *J. Exp. Med.* 176:1739–1744 (1992) and incorporated by reference herein, and encapsulation of the protein in lipid vesicles such as Novasome™ lipid vesicles (Micro Vescular Systems, Inc., Nashua, N.H.) may also be useful.

In any event, the antibody compositions of the present invention will thus be useful for treating or preventing infections caused by gram-positive bacteria and/or in reducing or eliminating the binding of gram-positive bacteria to host cells and/or tissues.

In accordance with the present invention, isolated and/or purified conserved amino acid sequences such as SEQ ID NOS 14–16 are provided which can be utilized in methods of treating or preventing a Gram-positive bacterial infection. Accordingly, in accordance with the invention, nucleic acids are provided which encode the peptide sequences of the invention and which encode the proteins which contain these conserved sequences, or degenerates thereof.

As indicated above, in accordance with the present invention, methods are provided for preventing or treating a Gram-positive bacterial infection which comprise administering an effective amount of an antibody to the peptides or proteins identified above in amounts effective to treat or prevent the infection. In addition, the antibodies in accordance with the invention are particularly effective against a wide range of Gram-positive bacteria because they can recognize conserved peptide sequences, and/or proteins containing these sequences therein, which will be found in the wide range of gram-positive bacteria that commonly cause infection in human or animal patients.

Accordingly, in accordance with the invention, administration of the antibodies of the present invention in any of the conventional ways described above (e.g., topical, parenteral, intramuscular, etc.), and will thus provide an extremely useful method of treating or preventing Gram-positive bacterial infections in human or animal patients. By effective amount is meant that level of use, such as of an antibody titer, that will be sufficient to either prevent adherence of the gram-positive bacteria, or to inhibit binding of the bacteria to host cells, and thus will be useful in the treatment or prevention of a gram-positive bacterial infection. As would be recognized by one of ordinary skill in this art, the level of antibody titer needed to be effective in treating or preventing a particular Gram-positive infection will vary depending on the nature and condition of the patient, and/or the severity of the pre-existing infection.

In addition to the use of the present antibodies to treat or prevent Gram-positive bacterial infection, the present invention contemplates the use of these antibodies in a variety of ways, including the detection of the presence of gram-positive bacteria to diagnose a bacterial infection, whether in a patient or on medical equipment which may also become infected. In accordance with the invention, a preferred method of detecting the presence of such infections involves the steps of obtaining a sample suspected of being infected by one or more Gram-positive bacteria species or strains, such as a sample taken from an individual, for example, from one's blood, saliva, tissues, bone, muscle, cartilage, or skin. While adequate diagnostic tests can be performed using the sample itself, it is also possible to perform more complex tests which utilize the DNA of the sample. In these diagnostic tests, the cells can then be lysed, and the DNA extracted, precipitated and amplified. Following isolation of the sample, diagnostic assays utilizing the antibodies of the present invention may be carried out to detect the presence of Gram-positive bacteria, and such assay techniques for determining such presence in a sample are well known to those skilled in the art and include methods such as radioimmunoasssay, Western blot analysis and ELISA assays. In general, in accordance with the invention, a method of diagnosing a Gram-positive bacterial infection is contemplated wherein a sample suspected of being infected with such bacteria has added to it an antibody in accordance with the present invention, and a Gram-positive bacterial infection will be indicated by antibody binding to the appropriate proteins or peptides in the sample.

Accordingly, antibodies in accordance with the invention may be used for the specific detection of gram-positive bacterial or surface proteins, for the prevention of infection from Gram-positive bacteria, for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies to the peptides and/or proteins of the present invention, including the products of an Fab immunoglobulin expression library. Accordingly, the invention contemplates the use of single chains such as the variable heavy and light chains of the antibodies as set forth above. Generation of any of these types of antibodies or antibody fragments is well known to those skilled in the art.

Any of the above described antibodies may be labeled directly with a detectable label for identification and quantification of Gram-positive bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

Alternatively, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. Similarly, the antibody may be conjugated to a hapten and the antibody-hapten conjugate detected using labeled anti-hapten antibody. These and other methods of labeling antibodies and assay conjugates are well known to those skilled in the art.

Further, when administered as pharmaceutical compositions to a wound or used to coat medical devices or polymeric biomaterials in vitro and in vivo, the antibodies of the present invention may be useful in those cases where there is a previous bacterial infection because of the ability of this antibody to further restrict and inhibit binding of Gram-positive bacteria to binding proteins such as fibrinogen or fibrin and thus limit the extent and spread of the infection. In addition, the antibody may be modified as necessary so that, in certain instances, it is less immunogenic in the patient to whom it is administered. For example, if the patient is a human, the antibody may be "humanized" by transplanting the complimentarity determining regions of the hybridoma-derived antibody into a human monoclonal antibody as described, e.g., by Jones et al., *Nature* 321:522–525 (1986) or Tempest et al. *Biotechnology* 9:266–273 (1991) or "veneered" by changing the surface exposed murine framework residues in the immunoglobulin variable regions to mimic a homologous human framework counterpart as described, e.g., by Padlan, Molecular lmm. 28:489–498 (1991), or European Patent application 519,596, these references incorporated herein by reference. Even further, when so desired, the monoclonal antibodies of the present invention may be administered in conjunction with a suitable antibiotic to further enhance the ability of the present compositions to fight bacterial infections.

Medical devices or polymeric biomaterials to be coated with the antibodies, proteins and active fragments described herein include, but are not limited to, staples, sutures, replacement heart valves, cardiac assist devices, hard and soft contact lenses, intraocular lens implants (anterior chamber or posterior chamber), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

It will be understood by those skilled in the art that the term "coated" or "coating", as used herein, means to apply the antibody or active fragment, or pharmaceutical composition derived therefrom, to a surface of the device, preferably an outer surface that would be exposed to a gram-positive bacterial infection. The surface of the device need not be entirely covered by the protein, antibody or active fragment.

In another embodiment of the invention, the antibodies may also be used as a passive vaccine which will be useful in providing suitable antibodies to treat or prevent a gram-positive bacterial infection. As would be recognized by one skilled in this art, such a vaccine may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle. However, the particular mode of administration will depend on the nature of the bacterial infection to be dealt with and the condition of the patient. The vaccine is preferably combined with a pharmaceutically acceptable carrier to facilitate administration, and the carrier is usually water or a buffered saline, with or without a preservative. The vaccine may be lyophilized for resuspension at the time of administration or in solution.

The preferred dose for administration of an antibody composition in accordance with the present invention is that amount which will be effective in preventing or treating a gram-positive bacterial infection, and one would readily recognize that this amount will vary greatly depending on the nature of the infection and the condition of a patient. As indicated above, an "effective amount" of antibody or pharmaceutical agent to be used in accordance with the invention is intended to mean a nontoxic but sufficient amount of the agent, such that the desired prophylactic or therapeutic effect is produced. As pointed out below, the exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using only routine experimentation. The dose should be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

When used with suitable labels or other appropriate detectable biomolecule or chemicals, the monoclonal antibodies described herein are useful for purposes such as in vivo and in vitro diagnosis of gram-positive bacterial infections or detection of gram-positive bacteria. Laboratory research may also be facilitated through use of such antibodies. Various types of labels and methods of conjugating the labels to the antibodies of the invention are well known to those skilled in the art, such as the ones set forth below.

For example, the antibody can be conjugated (directly or via chelation) to a radiolabel such as, but not restricted to, $^{32}$P, $^{3}$H, $^{14}$C, $^{35}$S, $^{125}$I, or $^{131}$I. Detection of a label can be by methods such as scintillation counting, gamma ray spectrometry or autoradiography. Bioluminescent labels, such as derivatives of firefly luciferin, are also useful. The bioluminescent substance is covalently bound to the protein by conventional methods, and the labeled protein is detected when an enzyme, such as luciferase, catalyzes a reaction with ATP causing the bioluminescent molecule to emit photons of light. Fluorogens may also be used to label proteins. Examples of fluorogens include fluorescein and derivatives, phycoerythrin, allo-phycocyanin, phycocyanin, rhodamine, and Texas Red. The fluorogens are generally detected by a fluorescence detector.

The location of a ligand in cells can be determined by labeling an antibody as described above and detecting the label in accordance with methods well known to those skilled in the art, such as immunofluorescence microscopy using procedures such as those described by Warren and Nelson (*Mol. Cell. Biol.*, 7: 1326–1337, 1987).

As indicated above, the antibodies of the present invention, or active portions or fragments thereof, are particularly useful for fighting or preventing bacteria infection in patients or on in-dwelling medical devices to make them safer for use. In short, the antibodies of the present invention are thus extremely useful in treating or preventing Gram-positive infections in human and animal patients and in medical or other in-dwelling devices.

In accordance with the invention, a diagnostic kit is also provided which utilizes an antibody of the invention as set forth above, and in one typical example, this kit may comprise an antibody of the invention which can recognize a conserved peptide region as set forth above or a protein containing said region, means for introducing the antibody to a sample suspected of containing gram-positive bacteria, and means for identifying gram-positive bacteria that are recognized by said antibody.

In accordance with the present invention, the peptides and proteins as described above may also be utilized in the development of vaccines for immunization against Gram-positive infections, and thus a method of eliciting an immune response in a human or animal is also provided wherein an immunogenic amount of a peptide or protein in accordance with the invention is administered to a human or animal. In the preferred embodiment, vaccines in accordance with the invention are prepared using methods that are conventionally used to prepare vaccines, and the preferred vaccine comprises an immunogenic amount of the peptides or proteins as described above along with a pharmaceutically acceptable vehicle, carrier or excipient. As would be recognized by one of ordinary skill in the art, these vaccines may be packaged for administration in a number of suitable ways, such as by parenteral (i.e., intramuscular, intradermal or subcutaneous) administration or nasopharyngeal (i.e., intranasal) administration. One such mode is where the vaccine is injected intramuscularly, e.g., into the deltoid muscle, however, the particular mode of administration will depend on the nature of the bacterial infection to be dealt with and the condition of the patient. The vaccine is preferably combined with a pharmaceutically acceptable vehicle, carrier or excipient in order to facilitate administration, and said carrier or other materials is usually water or a buffered saline, with or without a preservative. The vaccine may be lyophilized for resuspension at the time of administration or in solution.

The present invention thus provides for the identification and isolation of proteins having the signature conserved regions as set forth above, as well as the vaccines, antibodies and other forms of the invention as set forth above, and the invention will be particularly useful in developing and administering treatment regimens which can be used to fight or prevent infections caused by Gram-positive bacteria.

The following example is provided which exemplifies aspects of the preferred embodiments of the present invention. However, it will be appreciated by those of skill in the art that the techniques disclosed in the example which follow represent techniques discovered by the inventors to function well in the practice of the invention, and thus can be considered to constitute preferred modes for its practice. Moreover, those of skill in the art will also appreciate that in light of the present specification, many changes can be made in the specific embodiments which are disclosed and still obtain a like or similar result without departing from the spirit and scope of the invention

EXAMPLE

Identification and Isolation of Conserved Sequences and Proteins Containing them Gram-positive bacteria have a group of surface-located proteins that contain a unique sequence motif near the carboxyl termini. The motif consists of amino acid residues LPXTG (X being any amino acids) that is necessary for anchoring the protein to the bacterial cell wall by a transamidase called sortase. These bacterial surface proteins are thought to be important during the infection processes since they may mediate bacterial attachment to host tissues, and/or interact with the host immune system. They are potential candidates for active and/or passive immunization, as well as targets for new types of antibiotics. In *Staphylococcus aureus*, several of these proteins have been well characterized and were found to bind extracellular matrix proteins such as collagen, fibronectin, fibrinogen, as well as immunoglobulin G. The collagen and fibronectin binding proteins were shown to contribute to the virulence of *S. aureus* in animal models. In addition, immunization of mice with the collagen binding protein provided protection from septic death due to *S. aureus*, indicating that it may be used as a vaccine. LPXTG containing proteins that bind host proteins were also found in other gram-positive organisms such as *Enterococcus faecalis* and streptococci.

In this study we devised an algorithm for mining publicly available genome sequences of Gram-positive bacteria for LPXTG containing genes. We chose the genomes of *Staphylococcus aureus, Staphylococcus epidermidis, Enterococcus Faecalis, Streptococcus pyogenes, Streptococcus pneumoniae,* and *Streptococcus mutans,* all of which are important human pathogens. The genomes of four *S. aureus* strains were publicly available at the time of the analysis and were all included in the data mining process. The *S. aureus* genome sequences were obtained from the websites of The Institute for Genomic Research (TIGR) (strain COL), The Sanger Center (a methicillin resistant strain and a methicillin sensitive strain), and University of Oklahoma's Advanced Center for Genome Technology (OU-ACGT) (strain 8325). The genome sequences of *E. faecalis* (strain V583), *S. epidermidis* (strain RP62A) and *S. pneumoniae* Type 4 were obtained from TIGR, and the sequences of *S. mutans* and *S. pyogenes* (group A) were from OU-ACGT. Data mining was performed using a combination of software developed by us, Glimmer2 from TIGR and stand-alone BLAST from the National Center for Biotechnology Information. The system was set up on a Silicon Graphics machine running IRIX6.5. The algorithm consists the following steps: 1) process each sequence file which usually contains multiple contigs into individual files each of which consists one contig, 2) predict genes, 3) add unique identification tag to each predicted gene so that genes from different organisms can be put into one single database, 4) extract genes from each genome, 5) translate each gene into amino acid sequence, 6) form a blast searchable database of the protein sequences, and 7) blast search the database to find proteins that contain the LPXTG motif.

After LPXTG containing proteins were identified, they were collected into a subset and used to establish a separate blast searchable database. Each protein in this subset was blasted against each other as well as to the large protein database to identify LPXTG-containing proteins that are conserved among these organisms. Two groups were found. Members in each group exhibited substantial overall sequence homology with each other (see Tables 1 and 2 above). In addition, after multiple sequence alignment, there are stretches of completely identical sequences in each group (see FIGS. 1 and 2). Homology search with known genes indicated that the first group belongs to a family of cell division proteins, while the second group belongs to a family of amino acid transporters. However, none of the proteins in the two groups has been described for the organisms that we analyzed, and therefore they are novel for these bacteria.

Each protein in the two groups was examined for the presence of signal peptide through the SignalP mail server at Center for Biological Sequence Analysis, the Technical University of Denmark. Each was predicted to contain a signal peptide at the proper position, indicating that these are most likely surface proteins. Cell division proteins and amino acid transporters are important proteins for bacteria survival in vitro and in vivo. The fact that these proteins exhibit such high-level sequence conservation among the organisms suggests that they perform conserved functions. We envision that similar surface proteins are present in other Gram-positive bacteria. In fact we have identified 3 novel peptide sequences from the conserved proteins. The peptide sequences were selected from 3 regions in a *Staphylococcus aureus* protein that belongs to one ABC transporter group. Each region is highly conserved among the 6 Gram-positive bacteria examined (*Enterococcus faecalis, Staphylococcus epidermidis, Streptococcus pyogenes, Streptococcus mutans, Streptococcus pneumoniae,* and *Staphylococcus aureus*).

Also, in order to increase the chance that the sequences will be exposed on the surface, we limited the selection of the sequences to hydrophilic regions using the method of Kyte and Doolittle. The sequences are listed below:

SA-1: ALKTG KIDII ISGMT STPER KK (SEQ ID NO:14)
SA-2: VEGAVVEKPVAEAYL KQN (SEQ ID NO:15)
SA-3: EYAGV DIDLA KKIAK (SEQ ID NO:16)

The peptides were synthesized in an Advanced Chem Tech 396 multiple peptide synthesizer, using Fmoc chemistry and activation with HBTU. After cleavage from the resin, peptides were purified by reverse-phase chromatography on a Waters Delta-Pak C18 column, eluted-with gradient of acetonitrile in 0.1% trifluoroacetic acid/water. The purity of the peptides was further confirmed by mass spectrometry analysis.

The peptide-KLH conjugation with EDC: The carrier protein KLH and the peptides (1:1 by weight) were coupled using EDC (Pierce) for 2 hours at room temperature. The reaction mixture is subjected to a desalting column pre-equilibrated with the purification buffer (0.083 M sodium phosphate, 0.9 M NaCl, pH 7.2). The conjugated peptides were eluted with the purification buffer and 0.5 ml fractions were collected. Each fraction was measured for its absorbance at 280 nm and the fractions containing the conjugate were pooled.

The use of the conserved conjugated peptides and polypeptides: The principle, methods and applications described above for the three conjugated peptides are applicable and will be applied to proteins in the second group of highly homologous surface proteins. This evidenced that: 1) antibodies raised against these proteins will be able to recognize a wide range of Gram-positive bacteria and may be used as a basis for a broad spectrum passive immunization protocol; 2) protective, therapeutic, or diagnostic antibodies raised against these proteins could recognize conserved epitopes present on different species of Gram-positive bacteria; 3) a single mAb recognizing the conserved peptides could be used to protect against all Gram-positive bacterial infections; 4) these proteins may be used as a basis for a broad spectrum vaccine; and 5) these proteins may be used as novel targets for designing new types of antimicrobial agents.

What is claimed is:

1. An isolated amino acid sequence having a sequence selected from the group consisting of ALKTGKIDIIISGMTSTPERKK (SEQ ID NO: 14), VEGAVVEKPVAEAYLKQN (SEQ ID NO: 15), and EYAGVDIDLAKKIAK (SEQ ID NO: 16) and capable of generating an antibody that can recognize an amino acid sequence selected from the group consisting of SEQ ID NO: 14, SEQ ID NO: 15 and SEQ ID NO: 16.

2. An isolated surface protein from gram-positive bacteria which includes the sequence according to claim 1.

* * * * *